(12) United States Patent
Mitsuhashi

(10) Patent No.: US 9,719,129 B2
(45) Date of Patent: Aug. 1, 2017

(54) METHODS FOR ISOLATING VESICLES FROM BIOLOGICAL FLUIDS

(75) Inventor: Masato Mitsuhashi, Irvine, CA (US)

(73) Assignees: HITACHI CHEMICAL CO., LTD., Tokyo (JP); HITACHI CHEMICAL COMPANY AMERICA, LTD., San Jose, CA (US)

( * ) Notice: Subject to any disclaimer, the term of this patent is extended or adjusted under 35 U.S.C. 154(b) by 0 days.

(21) Appl. No.: 14/122,920

(22) PCT Filed: Jun. 10, 2011

(86) PCT No.: PCT/US2011/040076
§ 371 (c)(1),
(2), (4) Date: Nov. 27, 2013

(87) PCT Pub. No.: WO2012/170037
PCT Pub. Date: Dec. 13, 2012

(65) Prior Publication Data
US 2014/0099649 A1    Apr. 10, 2014

(51) Int. Cl.
*B01D 39/20* (2006.01)
*C12Q 1/68* (2006.01)
*C12N 15/10* (2006.01)

(52) U.S. Cl.
CPC ....... *C12Q 1/6806* (2013.01); *B01D 39/2017* (2013.01); *C12N 15/1003* (2013.01)

(58) Field of Classification Search
USPC ............................ 435/6.1, 6.12, 6.19, 317.1
IPC ........................ C12N 15/1003; B01D 39/2017
See application file for complete search history.

(56) References Cited

U.S. PATENT DOCUMENTS

| | | |
|---|---|---|
| 3,583,627 A | 6/1971 | Wilson |
| 4,895,706 A | 1/1990 | Root et al. |
| 4,925,572 A | 5/1990 | Pall |
| 5,139,685 A * | 8/1992 | de Castro .......... B01D 39/2017 210/435 |
| 5,647,990 A | 7/1997 | Vassarotti |
| 5,747,256 A | 5/1998 | Yan |
| 6,329,179 B1 | 12/2001 | Kopreski |
| 6,964,850 B2 | 11/2005 | Bevilacqua et al. |
| 7,741,023 B2 | 6/2010 | Mitsuhashi |
| 7,745,180 B2 | 6/2010 | Mitsuhashi |
| 9,012,615 B2 | 4/2015 | Mitsuhashi |
| 2002/0011450 A1 | 1/2002 | Kelly et al. |
| 2003/0203453 A1* | 10/2003 | Leonard ........................ 435/91.1 |
| 2004/0029124 A1 | 2/2004 | Zohlnhofer et al. |
| 2004/0072193 A1 | 4/2004 | Mitsuhashi |
| 2004/0203037 A1 | 10/2004 | Lo et al. |
| 2004/0258570 A1 | 12/2004 | Beebe et al. |
| 2004/0265864 A1 | 12/2004 | Mitsuhashi |
| 2006/0144790 A1* | 7/2006 | Kelly et al. .................... 210/650 |
| 2007/0254351 A1 | 11/2007 | Abrignani et al. |
| 2008/0009009 A1 | 1/2008 | Mitsuhashi |
| 2008/0015162 A1 | 1/2008 | Bhanot et al. |
| 2008/0025967 A1 | 1/2008 | Doi et al. |
| 2008/0188816 A1 | 8/2008 | Shimazaki et al. |
| 2008/0233573 A1 | 9/2008 | Storm et al. |
| 2008/0268429 A1 | 10/2008 | Pietrzkowski |
| 2009/0011410 A1 | 1/2009 | Mitsuhashi |
| 2009/0023149 A1 | 1/2009 | Knudsen |
| 2009/0149333 A1 | 6/2009 | Knudsen et al. |
| 2009/0258379 A1* | 10/2009 | Klein et al. .................. 435/7.92 |
| 2010/0113290 A1 | 5/2010 | Klass et al. |
| 2010/0196426 A1 | 8/2010 | Skog et al. |
| 2010/0203529 A1 | 8/2010 | Kuslich et al. |
| 2011/0195426 A1 | 8/2011 | Russo |
| 2011/0223583 A1 | 9/2011 | Gordon et al. |
| 2012/0211566 A1 | 8/2012 | Hensel et al. |
| 2012/0264628 A1 | 10/2012 | Okamoto et al. |
| 2013/0089855 A1 | 4/2013 | Mitsuhashi |
| 2013/0089864 A1* | 4/2013 | Mitsuhashi et al. ......... 435/6.11 |
| 2013/0172208 A1 | 7/2013 | Mitsuhashi |
| 2013/0337462 A1 | 12/2013 | Mergemeier |
| 2014/0148348 A1 | 5/2014 | Kuslich |
| 2014/0148350 A1 | 5/2014 | Spetzler |
| 2014/0194613 A1 | 7/2014 | Skog |
| 2015/0141634 A1 | 5/2015 | Mitsuhashi |
| 2015/0275301 A1 | 10/2015 | Mitsuhashi et al. |

(Continued)

FOREIGN PATENT DOCUMENTS

| | | |
|---|---|---|
| JP | 1997-067336 | 3/1997 |
| WO | 93/19831 A1 | 10/1993 |

(Continued)

OTHER PUBLICATIONS

Jan. 10, 2012 ISR/WO from related PCT App No. PCT/US2011/40076.
Jan. 17, 2014 ISR/WO from related PCT App No. PCT/US2013/063122.
Mar. 11, 2014 ISR/WO from related PCT App No. PCT/US2013/063114.
Barnett, A et al., Angiotensin-Receptor Blockade Versus Converting-Enzyme Inhibition in Type 2 Diabetes and Nephropathy, New Eng J, Nov. 4, 2004, vol. 351, pp. 1952-61.
Chen et al., Microfluidic isolation and transcriptome analysis of serum microvesicles, Lab Chip, 2010, 10, pp. 505-511.
Haas et al., Patient Characteristics Associated With Successful Mobilizing and Autografting of Peripheral Blood Progenitor Cells in Malignant Lymphoma, Blood, vol. 83, No. 12, Jun. 15, 1994, pp. 3787-3794.

(Continued)

*Primary Examiner* — Ralph Gitomer
(74) *Attorney, Agent, or Firm* — Knobbe Martens Olson & Bear LLP

(57) ABSTRACT

Provided is a device that collects vesicles and vesicle-like materials from biological fluids. Such devices comprise at least one sample loading region; at least one corresponding vesicle-capture material, wherein said vesicle-capture material comprises glass-like materials; and at least one corresponding sample receiving region, wherein passage of the biological fluid from the sample loading region through the vesicle capture material and into the sample receiving region results in the capture of vesicles. Additional methods provide for a method of isolating vesicles and vesicle-like materials from biological fluids are also provided.

9 Claims, 16 Drawing Sheets

(56) References Cited

U.S. PATENT DOCUMENTS

| | | |
|---|---|---|
| 2016/0074860 A1 | 3/2016 | Mitsuhashi |
| 2016/0122823 A1 | 5/2016 | Mitsuhashi |
| 2016/0222456 A1 | 8/2016 | Yamamoto et al. |

FOREIGN PATENT DOCUMENTS

| | | |
|---|---|---|
| WO | WO 02/57414 | 7/2002 |
| WO | WO 2006/045053 | 4/2006 |
| WO | WO 2008/092993 | 8/2008 |
| WO | WO 2009/015357 | 1/2009 |
| WO | WO 2009/057695 | 5/2009 |
| WO | WO 2009/070442 | 6/2009 |
| WO | WO 2009/100029 | 8/2009 |
| WO | WO 2010/056337 | 5/2010 |
| WO | WO 2010/086163 | 8/2010 |
| WO | 2011100458 A2 | 8/2011 |
| WO | 2011156763 | 12/2011 |
| WO | WO 2011/156734 | 12/2011 |
| WO | WO 2013/043922 | 3/2013 |
| WO | WO 2013/134786 | 9/2013 |
| WO | 2014055687 | 4/2014 |
| WO | 2014182330 | 11/2014 |

OTHER PUBLICATIONS

Hotfilder et al., Def-2,-3,-6 and -8, novel mouse genes differentially expressed in the haemopoietic system, Brit J Haematology, 1999, 106, pp. 335-334.

Ito et al., Myeloid Reconstitution—Serum stem cell growth factor for monitoring hematopoietic recovery following stem cell transplantation, Bone Marrow Transplantation, 2003, 32, pp. 391-398.

Wellman et al., Detection of differentially expressed genes in lymphomas using cDNA arrays: identification of clusterin as a new diagnostic marker for anaplastic large-cell lymphomas, Blood, Jul. 15, 2000, 96(2), pp. 398-404.

Zheng, M et al., Urinary Podocyte-Associated mRNA profile in Various Stages of Diabetic Nephropathy, PLOS One, May 31, 2011, vol. 6, pp. 1-7.

Gene Cards DEFA3 Gene, first internet archive Aug. 7, 2010, p. 1-14.

Tomblyn et al., Guidelines for preventing infectious complications among hematopoietic cell transplantation recipients: A global prespective, Biol Blood Marrow Transplant, 15:1143-1238 (2009).

Zucker et al., Immature platelet fraction as a predictor of platelet recovery following hematopoietic progenitor cell transplantation, Laboratory Hematology, 12:125-130 (2006).

Shawn M. Ferguson, et al., "Vesicular Localization and Activity-Dependent Trafficking of Presynaptic Choline Transporters", The Journal of Neuroscience, Oct. 29, 2003, pp. 9697-9699.

Kevin C. Miranda, et al., "Nucleic acids within urinary esosomes/microvesicles are potential biomarkers for renal disease", International Society of Nephrology, Kidney International (2010) 78, pp. 191-199.

Hubert Rehm, "Binding Assays with Membranes", 2.2 Binding, Protein Biochemistry and Proteomics, Elesevier, pp. 37-39.

Jorge D. Erusalimsky, et al., "A Glass Fiber/Diethylaminoethyl Double Filter Binding Assay That Measures Apoptotic Internucleosomal DNA Fragmentation", Analytical Biochemistry, vol. 242, 1996, pp. 187-196.

Taku Murakami, et al., Development of Glomerulus-, Tubule-, and Collecting Duct-Specific mRNA Assay in Human Urinary Exosomes and Microvesicles, PLOS ONE, vol. 9, Oct. 2014, pp. 1-10.

Mar. 9, 2015 Partial European Search Report for PCT/US2011/040076, Application No. 11867123.9, 9 pgs.

Anita Cheruvanky, et al., "Rapid isolation of urinary exosomal biomarkers using a nanomembrane ultrafiltration concentrator", American Journal of Physiol Renal Physiol, vol. 292, May 2007, pp. F1657-F1661.

Bio Scientific, "ExoMir Kit Manual", Catalog 5145, www.yumpu.com/en/document/view/30138118/exomirtm-kit-manual-nordic-biosite/2, Feb. 17, 2015.

Mathivanan et al., Exosomes: Extracellular Organelles Important in Intercellular Communication, J of Proteomics 73(10)1907-20 (2010).

"Binding Assays with Membranes," Jan. 1, 2006, Protein Biochemistry and Protoeomics, Elsevier, pp. 37-39.

Absolute Quantitation Using Standard Curve Getting Guide, Applied Biosystems, pp. i-viii and 1-80, Jun. 2010, printed from http://www3.appliedbiosystems.com/cms/groups/mcb_support/documents/generaldocuments/cms_032176.pdf.

Arteaga et al., Endothelial microparticles and platelet and leukocyte activation in pateints with the metabolic symdrome, Am J Cardiol, vol. 98:70-74 (2006).

Bachmann et al., Renal effects of Tamm-Horsfall protein (uromodulin) deficiency in mice, Am J Physiol, Renal Physiol, 288:F559-567 (2005).

Bakris, Gl., Recognition, pathogenesis, and treatment of different stages of nephropathy in patients with type 2 diabetes mellitus. Mayo Clinc Proceedings, vol. 86, No. 5, pp. 444-456, May 2011.

Beltrami, et al.: "Analysis of urinary microRNAs in chronic kidney disease: Figure1," Biochemical Society Transactions, vol. 12, No. 4, Aug. 1, 2012, pp. 4-879.

Conde-Vancells et al., Candidate biomarkers in exosome-like vesicles purified from rat and mouse urine samples, Proteomics Clin Appl 4(4):416-25 (2010).

Cutillas et al., The urinary proteome in Fanconi syndrome implies specificity in the reabsorption of proteins by renal proximal tubule cells, Am J Physio Renal Physiol (2004) vol. 287(3):353-364.

Dennis et al., Identification from public data of molecular markers of adenocarcinoma characteristic of the site of origin, Cancer Res, vol. 62(21):5999-6005 (2002).

Enard et al., Intra- and Interspecific Variation in Primate Gene Expression Patterns, Science (2002) vol. 296:340.

Ferguson et al.: Vesicular Localization and Activity-Dependent Trafficking of Presynaptic Choline Transponders, The Journal of Neuroscience, Oct. 29, 2003, 23(30):9697-9709.

Golub, et al.: "Molecular Classification of Cancer: Class Discovery and Class Prediction by Gene Expression Monitoring," Science, vol. 286, pp. 531-537, Oct. 1999.

Gonzales et al., Large-scale proteomics and phosphoproteomics of urinary exosomes, J Am Soc Nephrol, 20(2):363-79 (2009).

Gonzales et al., Chapter 6: Isolation and Purification of Exosomes in Urine in Alex J. Rai (ed.), The Urinary Proteome: Methods and Protocols, Methods in Molecular Biology, vol. 641, pp. 89-99, 2010.

Grant et al., A filtration-based protocol to isolate human plasma membrane-derived viscles and exosomes from blood plasma. Journal of Immunocological Methods, vol. 371, pp. 143-151, Jun. 30, 2011.

Guo et al., Surfactant protein gene A, B, and D marker alleles in chronic obstructive pulmonary disease of a Mexican population, Eur Respir J, 18(3):482-90 (2001).

Harada and Mitsuhashi, "Assessment of post-transplant kidney function by measuring glomerulus and tubule specific mRNAs in urine exosome," American Journal of Transplantation, vol. 12, Supp. 3, pp. 369-370, Abstract No. 1158, May 2012.

Hashem, Biochemical and expression studies on Acquaporin 9 (AQP9) in wild and AQP9 knockout mice, Veterinarski Archiv (2010) vol. 80(1):93-112.

Hewitt et al., Discovery of Protein Biomarkers for Renal Diseases, J Am Soc Nephrol (2004) vol. 15(7):1677-1689.

Hoorn et al., Prospects for urinary proteomics: exosomes as a source of urinary biomarkers, Nephrology, 10:283-290 (2005).

Hunter et al., Detection of microRNA expression in human peripheral blood microvesicles, PLoS One 3:e3694 (2008).

Jimenez et al., Endothelial microparticles released in thrombotic thrombocytopenic purpura express von Willibrand factor and markers of endothelial activation, Br J Haemat (2003) vol. 123(5):896-902.

Keller et al., "Body fluid derived exosomes as a novel template for clinical diagnostics," Journal of Translational Medicine, vol. 9, 86, Jun. 2011, printed as pp. 1/9-9/9.

(56) References Cited

OTHER PUBLICATIONS

Klein et al., Ex-Vivo Assessment of Candidate Anti-Inflammatory Agents in the Treatment of Gram Negative Sepsis, Immun & Infec Dis (1994) vol. 4(1):33-35.
Koga et al., Purification, characterization and biological significance of tumor-derived exosomes, Anticancer Res, 25(6A):3703-7 (2005).
Labsource: Whatman Glass Microfiber Filters, printed from internet Dec. 12, 2009 2011:<URL:http://www.labsource.com/Catalog/Group.aspx?GroupID=82>] pg. 1.
Lescuyer et al., Proteomics: Clinical Applications (2008) vol. 2(7-8):1008.
Lucendo et al., Treatment with topical steroids downregulates IL-5, eotaxin-1/CCL11, and eotaxin-3/CCL26 gene expression in eosinophilic esophagitis, Am J Gastro 103(9):2184-93 (2008).
Luo et al., Rantes stimulates inflammatory cascades and receptor modulation in murine astrocytes, 39(1):19-30 (2002).
Mathivanan, et al.: "ExoCarta 2012: database of exosomal proteins, RNA and lipids," Nucleic Acids Research, vol. 40, No. D1, Oct. 11, 2011, pp. D1241-D1244.
Mitchell et al., Can urinary exosomes act as treatment response markers in prostate cancer? J Transl Med, 12:7:4 (2009).
Muller, Gunter: "Microvesicles/exosomes as potential novel biomarkers of metabolic diseases," Diabetes, Metabolic Syndrom and Obesity: Targets and Therapy, Aug. 1, 2012, p. 247.
Nilsson et al., Prostate cancer-derived urine exosomes: a novel approach to biomarkers for prostate cancer, Br J Cancer 100:1603-1607 (2009).
Notterman et al., in Microarrays and Cancer Research (2002) Warrington et al. (eds.) pp. 81-111 at pp. 81-82.
Olszewska-Pazdrak et al., Cell-specific expression of Rantes, MCP-1, and MIP-1 alpha by lower airway epithelial cells and eosinophils infected with respiratory syncytial virus, J Virol, 72(6):4756-64 (1998).
Pisitkun et al., Discovery of urinary biomarkers, Mol Cell Proteomics, 5(10):1760-71 (2006).
Pisitkun et al., Identification and proteomic profiling of exosomes in human urine, Proc Natl Acad Sci USA, 101:13368-73 (2004).
Post et al., Demonstration of the presence of independent pre-osteoblastic and pre-adipocytic cell populations in bone marrow-derived mesenchymal stem cells, Bone, 43(1):32-9 (2008).
Pusztai et al.: "Clinical trial design for microarray predictive marker discovery and assessment," Annals of Oncology 15: 1731-1737, 2004.
Rappa et al., The stem cell-associated antigen CD133 (Prominin-1) is a molecular therapeutic target for metastatic melanoma, Stem Cells, 26:3008-17 (2008).
Sartorius Stedim Biotech., Ultrafiltration & Protein Purification Products. Fisher Scientic, pp. 1-96, Mar. 2011.
Sellam et al., Increased levels of circulating microparticles in primary Sjögren's syndrome, systemic lupus erythematosus and rheumatoid arthritis and relation with disease activity, Arthritis Res Ther 11(5):R156 (2009).
Simpson et al., Proteomic profiling of exosomes: current perspectives, Proteomics 8(19):4083-99 (2008).
Smalley et al., Isolation and identification of potential urinary microparticle biomarkers of bladder cancer, J Proteome Res 7:2088-96 (2008).
Stahlberg et al., Properties of the reverse transcription reaction in mRNA quantification. Clinical Chemistry, vol. 50, No. 3, pp. 509-515, 2004.
Strausberg et al., Reading the Molecular Signatures of Cancer, Microarrays & Cancer Res (2002) pp. xi-xvi.
Taylor et al., MicroRNA signatures of tumor-derived exosomes as diagnostic biomarkers of ovarian cancer, Gynecol Oncol 110(1):13-21 (2008).
Thery et al., Isolation and characterization of exosomes from cell culture supernatants and biological fluids, Chapter 3, Curr Protoc Cell Biol, Unit 3.22 (2006).
Tockman et al., Considerations in bringing a cancer biomarker to clinical application, Cancer Res 1:52(9Suppl):2711s-2718s (1992).
Vaes et al., Comprehensive microarray analysis of bone morphogenetic protein 2-induced osteoblast differentiation resulting in the identification of novel markers for bone development, J Bone Miner Res 17(12):2106-18 (2002).
Van Niel et al., Exosomes: a common pathway for a specialized function, J Biochem 140(1):13-21 (2006).
Van't Veer et al., Enabling personalized cancer medicine through analysis of gene-expression patterns, Nature 452(7187):564-70 (2008).
Whitehead et al., Variation in tissue-specific gene expression among natural populations, Genome Biol 6(2):R13 (2005).
Xu et al., Gene expression in peripheral blood differs after cardioembolic compared with large—vessel atherosclerotic stroke: biomarkers for the etiology of ischemic stroke, JCBFM (2008) vol. 28:1320-1328.
Zefon International. Glass Fiber Filters, Jan. 14, 2010 (printed from internet Oct. 7, 2011) <http://web.archive.org/web/20100114112921/http://www.zefon.com/store/glass-fiber-filters/>].
Zhou et al., Urinary exosomal transcription factors, a new class of biomarkers for renal disease, Kidney Intl (2008) vol. 74(5):613-621.
Mar. 9, 2015 European Partial Supplementary Search Report, re 11867123.9 (PCT/US2011040076).
Dec. 10, 2013 IPRP/WO from related PCT App No. PCT/US2011/040076.
Japanese Office Action (Notice of Reason for Rejection) re JP Application No. 2014-51443, mailed May 19, 2015.
May 11, 2016, European Extended Search Report re EP Application No. 13844293.4.
Aug. 23, 2016, Japanese Office Action (Notice of reason for Rejection) re JP Application No. 2015-535767.
Jan. 29, 2015 IPRP from related PCT App No. PCT/US13/63122.
Dec. 2, 2015 Office Action from related Chinese App No. 2013800523722.
Nov. 10, 2015 ISR/WO from related PCT App No. PCT/US2013/063114.

* cited by examiner

A - Glassfiber
B - Nitrocellulose (NC)
C - Nylon (Nytran) Polyvinylidene difluoride (PVDF)
D - Immobilon P
E - Nano alumina fibers
F - Polystrene
G - Ethylene vinyl acetate
H - Silk
I - Alginate
J - PolyNZPA
K - Leukocyte capture membrane

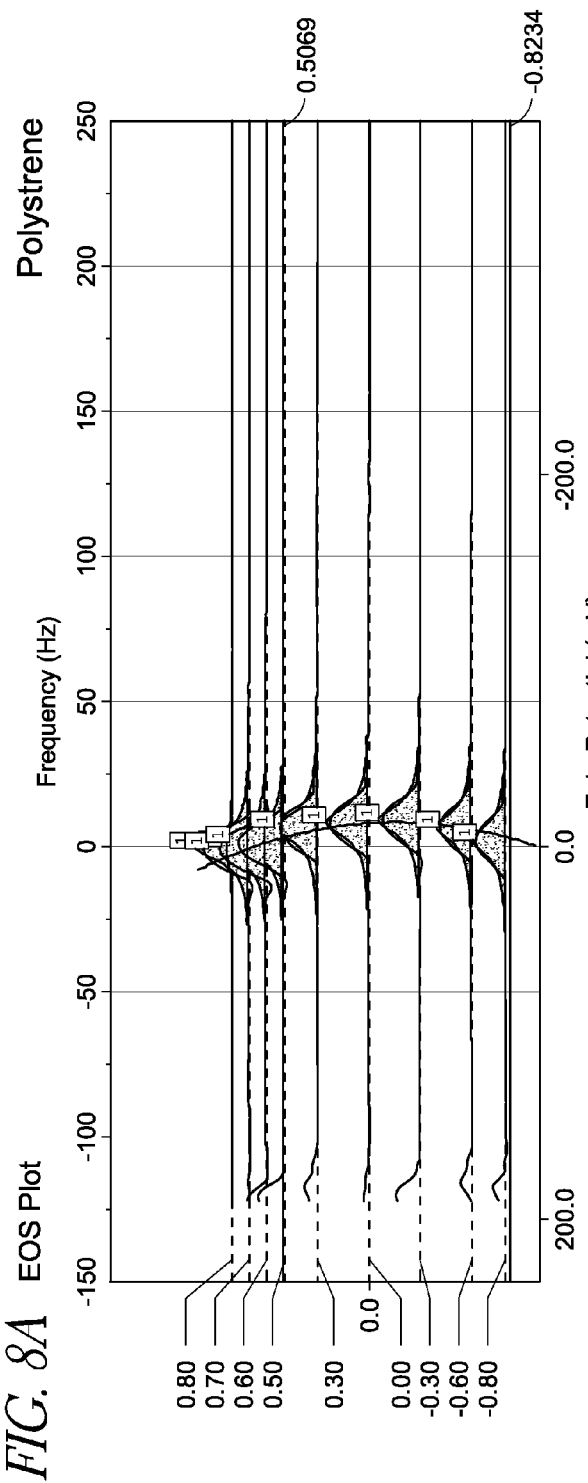
FIG. 8A  EOS Plot

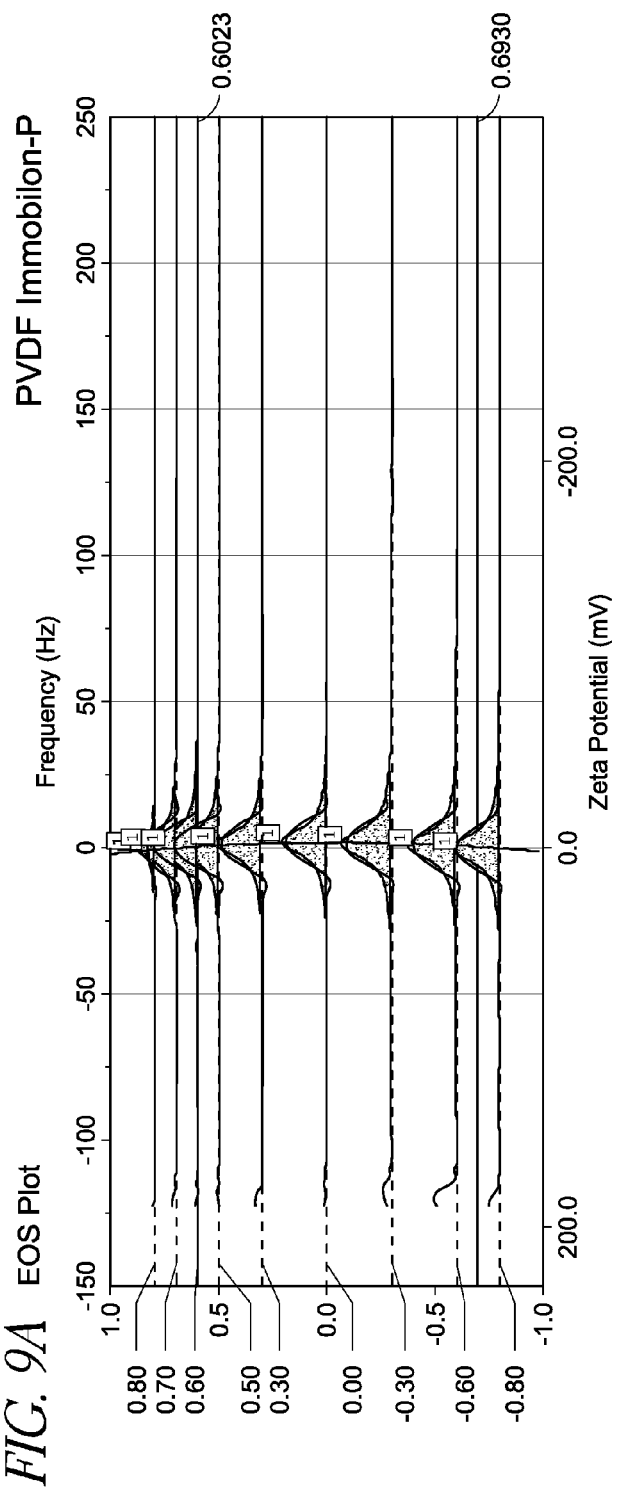
FIG. 9A  EOS Plot

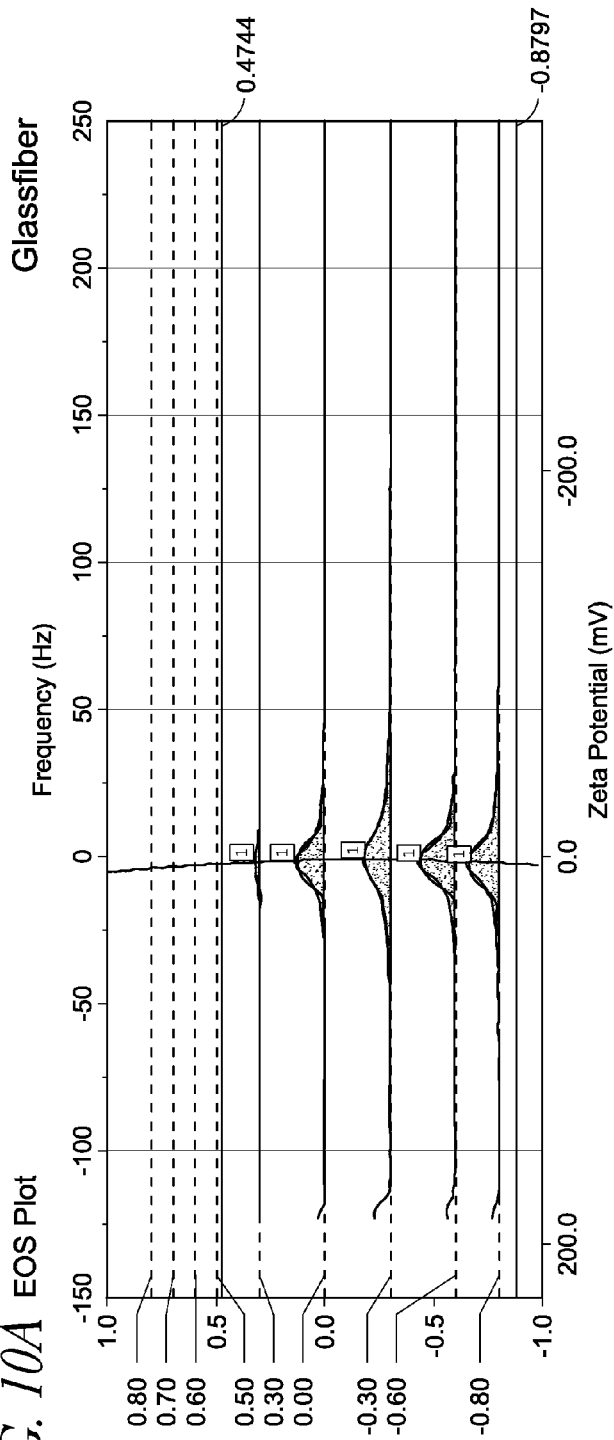
FIG. 10A EOS Plot

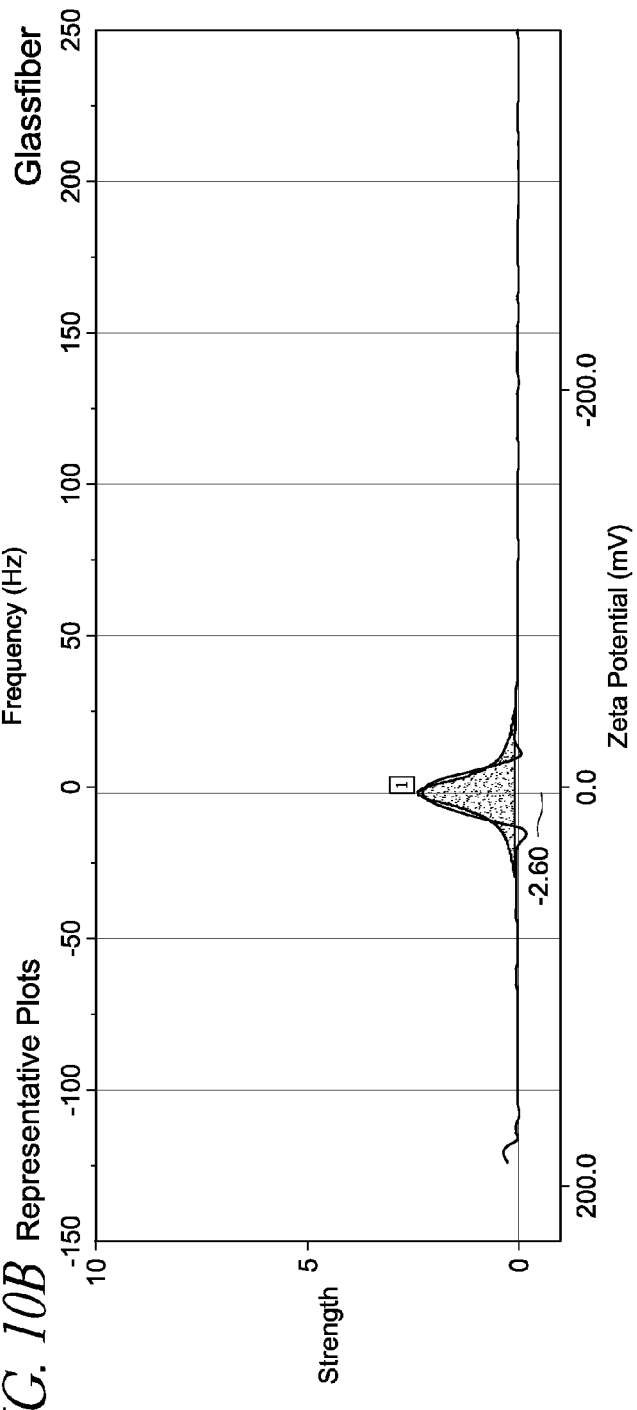
FIG. 10B Representative Plots

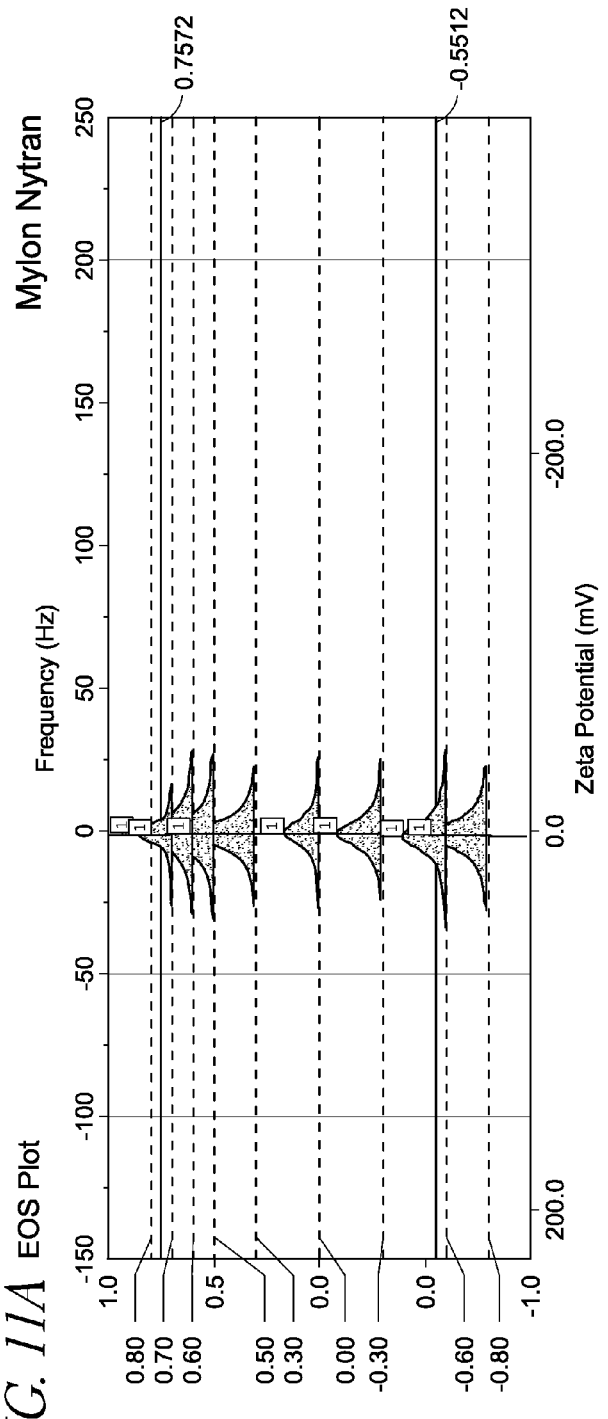
FIG. 11A EOS Plot

METHODS FOR ISOLATING VESICLES FROM BIOLOGICAL FLUIDS

This application is the U.S. National Stage under 35 U.S.C. §371 of International Application No. PCT/US2011/040076, filed Jun. 10, 2011. The contents of the priority applications listed in the accompanying Application Data Sheet are incorporated in their entirety by reference herein.

BACKGROUND

Field of the Invention

The present disclosure relates to compositions, devices, and methods for capture of exosomes, vesicles, and other circulating membrane bound nucleic acid and/or protein-containing structures that are released from cells into biological fluids.

Description of Related Art

Currently, many diagnostic tests are performed on a biological fluid sample (e.g., blood, urine, etc.) extracted from a patient for the diagnosis or prognosis of disease. The diagnosis or prognosis may be derived from identification of a biomarker or a biochemical pattern that is not present in healthy patients or is altered from a previously obtained patient sample. However, these diagnostic tests are typically based upon the presence of known and well characterized biomarkers in the fluid sample (e.g., electrolytes, urea, creatinine, glucose, plasma proteins such as albumins, immunoglobulins and the like, biological compounds such as thiamin, riboflavin, niacin, vitamin B6, folic acid, vitamin D, biotin, or iron). Some diagnostic tests are directed to detection of specific biomarkers (e.g., cell surface proteins) that are unique to diseased cells. Some diagnostic tests are designed to detect or identify disease states through the isolation and amplification of nucleic acids, in order to study expression levels of certain disease-associated genes.

Often, use of bodily fluids to isolate or detect biomarkers significantly dilutes a biomarker and results in readouts that lack the requisite sensitivity. Additionally, most biomarkers are produced in low or even moderate amounts in tissues other than the diseased tissue, such as normal tissues. Thus, there exists a need for improved sensitivity and accuracy in diagnostic assays that employ biological fluids such as bodily fluids.

SUMMARY

Given the need for diagnostic assays that employ biological fluids, and in particular those that exploit certain biomarkers within such fluids that are vesicle bound, there is provided, in several embodiments, a method of isolating vesicles from biological fluid, comprising obtaining a biological sample comprising the vesicles, loading at least a portion of the biological sample into a sample loading region of a vesicle capture device, passing the biological fluid sample from the sample loading region through a vesicle-capture material in the vesicle capture device, the vesicle-capture material comprising glass-like materials to produce a supernatant; and passing the supernatant to a sample receiving region of the vesicle capture device and discarding the supernatant, wherein the passings results in capture of the vesicles within the biological fluid on or in the vesicle-capture material.

In several embodiments, the vesicle-capture material comprises glass-like materials. In several embodiments the vesicle-capture material comprises a plurality of layers of the material. In some embodiments, the retention rate of the vesicle-capture material is greater than 50%, 75%, 90% or 99% for vesicles having a diameter of from about 0.6 microns to about 1.5 microns in diameter. In one embodiment, the vesicle-capture material captures vesicles sized from about 0.7 microns to about 1.6 microns in diameter. In one embodiment, the vesicle-capture material captures exosomes or other vesicles ranging in size from about 0.020 to about 1.0 microns.

In several embodiments, combinations of vesicle capture materials are used. In some embodiments, a plurality of glass-like materials are used. In several embodiments, a plurality of layers of materials are used. In several embodiments, the plurality of layers of the vesicle-capture material comprises at least a first layer and a second layer of glassfiber. In some embodiments, the biological fluid is passed through the first layer of glassfiber so as to capture material from the biological sample that is about 1.6 microns or greater in diameter. In some embodiments, the biological fluid is passed through the second layer of glassfiber so as to capture vesicles having a minimum size from about 0.6 microns to about 0.8 microns in diameter, and having a maximum size of less than 1.6 microns. In several embodiments, combinations of glass-like and non-glass-like materials are used. In one embodiment, a non glass-like material comprising nitrocellulose is used in combination with a glass-like material.

In several embodiments, the vesicle-capture material is modified in order to tailor the profile of vesicles that are captured. In one embodiment, the zeta potential of the material is used as a basis for modification (e.g., electrostatic charging) of the material. In several embodiments, the material (based on its zeta potential) does not require modification.

In several embodiments, the methods disclosed herein further comprise eluting the vesicles from the vesicle-capture material. As such, in some embodiments, the vesicle-capture material is optimized to balance the attractive nature of the material and the ability of the material to release captured vesicles.

In several embodiments, the vesicle-capture device can be connected to a vacuum source in order to pass the biological fluid from the sample loading region through the vesicle-capture material and into the sample receiving region. In one embodiment, the passings are accomplished through the application of vacuum pressure to the device. In several embodiments, the vesicle-capture device can receive positive pressure in order to pass the biological fluid from the sample loading region through the vesicle-capture material and into the sample receiving region. In one embodiment, the passings are accomplished through the application of positive pressure to the device. In several embodiments, the device can be placed in a centrifuge in order to pass the biological fluid from the sample loading region through the vesicle-capture material and into the sample receiving region. In one embodiment, the passings are accomplished through low-speed centrifugation of the device. In several embodiments, the vesicle capture device is configured in a multi-well plate format.

There is also provided herein a method for isolating a biomarker, comprising isolating vesicles comprising at least one biomarker from a biological fluid by passing the biological fluid through a vesicle-capture material, removing non-vesicle material from the vesicle-capture material and lysing the vesicles in or on the vesicle-capture material with a lysis buffer, thereby isolating a biomarker from the vesicles.

In some embodiments, the biomarker is selected from the group consisting of RNA, DNA, protein, and carbohydrate. In several embodiments, the RNA is of a type selected from the group consisting of mRNA, miRNA, rRNA, tRNA, and vRNA.

There is also provided, in several embodiments, a vesicle capture device comprising a biological fluid sample loading region, a vesicle-capture material comprising at least a first and a second layer of glassfiber, wherein the first layer is closer to the sample loading region than the second layer, wherein the first layer of glassfiber captures material from the biological sample that is about 1.6 microns or greater in diameter, wherein the second layer of glassfiber captures vesicles having a minimum size from about 0.6 microns to about 0.8 microns in diameter, and having a maximum size of less than 1.6 microns; and a biological fluid sample receiving region, wherein passing of the biological fluid sample from the sample loading region to the sample receiving region results in capture of vesicles within the biological fluid sample on or in the vesicle-capture material.

In one embodiment, the vesicle-capture device is configured to be connected to a vacuum source in order to pass the biological fluid sample from the sample loading region through the vesicle-capture material and into the sample receiving region. In one embodiment, the vesicle-capture device is configured to receive positive pressure in order to pass the biological fluid sample from the sample loading region through the vesicle-capture material and into the sample receiving region. In one embodiment, the device is configured to be placed in a centrifuge in order to pass the biological fluid sample from the sample loading region through the vesicle-capture material and into the sample receiving region.

Some embodiments provide a device for the collection of vesicles from a biological fluid, the device comprising (1) at least one sample loading region; (2) at least one corresponding vesicle-capture material and (3) at least one corresponding sample receiving region, wherein passage of the biological fluid from the sample loading region through the vesicle-capture material and into the sample receiving region results in capture of vesicles within the biological fluid on or in the vesicle-capture material. In some embodiments, wherein the vesicle-capture material comprises glass-like materials, which have a structure that is disordered or "amorphous" at the atomic scale, like plastic or glass. Glass-like materials include, but are not limited to glass beads or fibers, silica beads (or other configuration), nitrocellulose, nylon, polyvinylidene fluoride (PVDF) or other similar polymers, metal or nano-metal fibers, polystyrene, ethylene vinyl acetate or other co-polymers, natural fibers (e.g., silk), alginate fiber, poly NZPA, or combinations thereof. In certain embodiments, the vesicle-capture material optionally comprises a plurality of layers of vesicle-capture material. In other embodiments, the vesicle-capture material further comprises nitrocellulose. In some embodiments, the vesicle-capture material captures exosomes ranging in size from about 50 to about 100 nanometers.

In some embodiments, the device is comprises a multi-well plate format. In other embodiments, the device is can be placed in a centrifuge in order to pass the biological fluid from the sample loading region through the vesicle-capture material and into the sample receiving region. In some embodiments, the device is can be connected to a vacuum source in order to pass the biological fluid from the sample loading region through the vesicle-capture material and into the sample receiving region. In other embodiments, the device can receive positive pressure in order to pass the biological fluid from the sample loading region through the vesicle-capture material and into the sample receiving region. In still additional embodiments, the passage of the biological fluid into the sample receiving region is achieved by gravity pressure or in other embodiments by wicking-type materials.

Some embodiments provide a method of isolating vesicles from biological fluid, comprising (1) obtaining a biological sample comprising vesicles; (2) loading at least a portion of the biological sample into a sample loading region of a vesicle capture device; (3) passing the biological sample from the sample loading region through a vesicle-capture material in the vesicle capture device, the vesicle-capture material comprising glass-like materials; and (4) passing the biological sample from the vesicle-capture material to a sample receiving region of the vesicle capture device, wherein the passages of the biological sample results in capture of the vesicles within the biological fluid on or in the vesicle-capture material. In some embodiments, the vesicle-capture material further comprises nitrocellulose. In other embodiments, the method further comprises eluting the vesicles from the vesicle-capture material. In some embodiments, the passing is accomplished through the application of vacuum pressure to the device. In other embodiments, the passing is accomplished through low-speed centrifugation of the device. In some embodiments, the method further comprises capturing, enriching, and/or condensing vesicles comprising RNA; removing non-vesicle material from the device; and lysing the vesicles in or on the vesicle-capture material with a lysis buffer, thereby isolating vesicle-associated RNA from the vesicles.

BRIEF DESCRIPTION OF THE FIGURES

FIGS. 8A-8B depict the determination of the zeta potential of polystyrene.

FIGS. 9A-9B depict the determination of the zeta potential of PVDF Immoblion-P.

FIGS. 10A-10B depict the determination of the zeta potential of glassfiber.

FIGS. 11A-11B depict the determination of the zeta potential of mylon nytran.

DETAILED DESCRIPTION

Figure 1A:
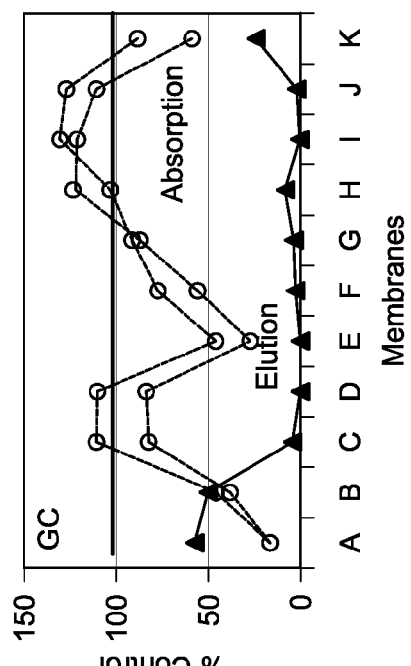
FIGS. 1A-1F depict screening of various filters for their exosomal capture efficiency.
Figure 1B:
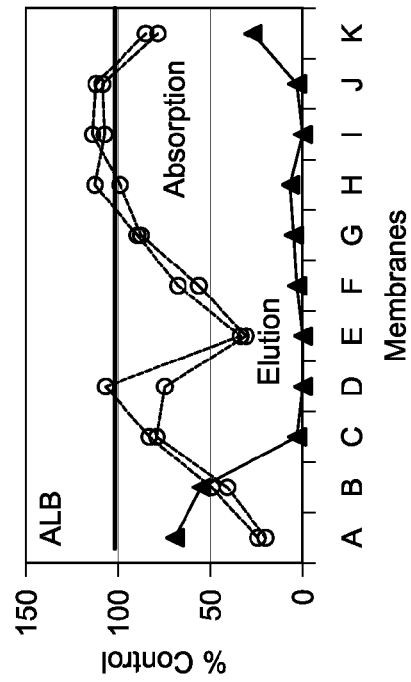
Figure 1C:
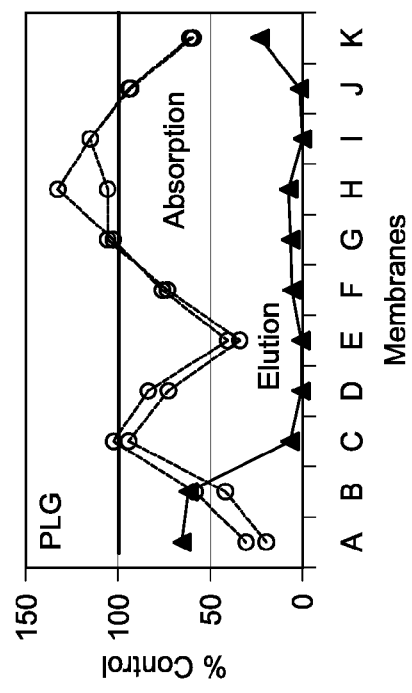
Figure 1D:
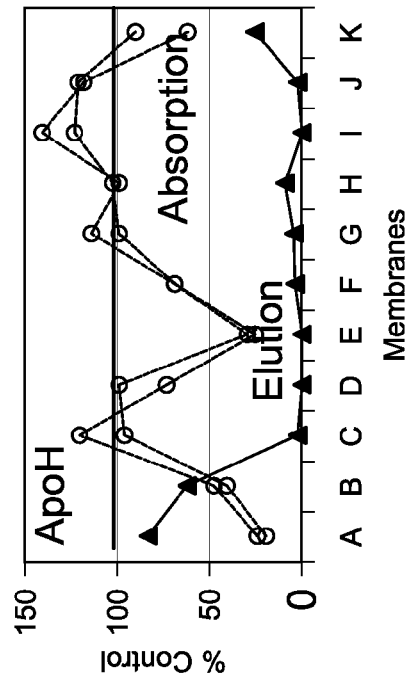
Figure 1F:
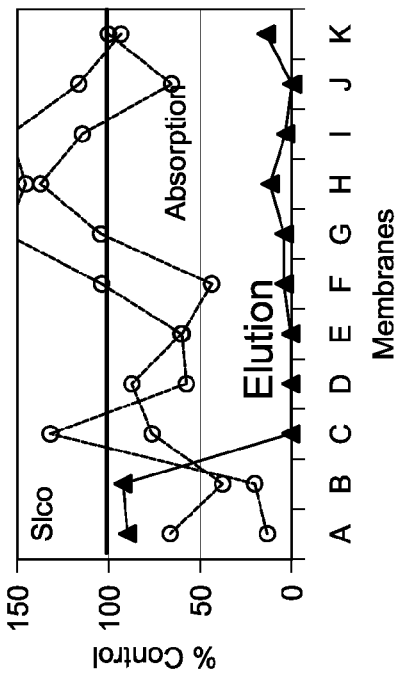
Figure 1E:
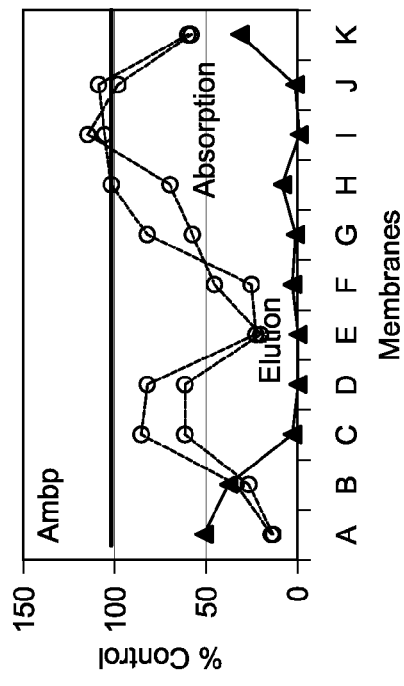

Identification of specific biomarkers including, but not limited to, DNA, RNA (such as mRNA, miRNA or micro-RNA, and siRNA), and proteins can provide bio-signatures that are used for the diagnosis, prognosis, or theranosis of a condition or disease. See, e.g., Jiang Q., Wang Y., Hao Y., Juan L., Teng M., Zhang X., Li M., Wang G., Liu Y., (2009) miR2Disease: a manually curated database for microRNA deregulation in human disease. *Nucleic Acids Res* 37:D98-104, which is incorporated herein by reference. While DNA and RNA typically are contained in the intracellular environment, these nucleic acids also exist extracellularly. In some cases, DNA and/or RNA are naked (e.g., not encapsulated or associated with another structure or compound.) RNAses, which degrade RNA, are known to be elevated in some disease states, for example, in certain cancers. The extracellular environment, including the plasma, serum, urine, or other biological fluids is known to contain substantial quantities of RNAses. Given this context, extracellular DNA, RNA, or other biomarkers are often considered a meaningless degradation product in an extracellular sample, not only because their levels may not be representative of the true levels of the intracellular message, but also due to the instability and poor quality of the nucleic acids.

Moreover, due to the rapid rate of nucleic acid degradation in the extracellular environment, conventional understanding suggests that many tissues are unable to provide nucleic acid that would be suitable as a diagnostic target, because the nucleic acids would be degraded before they could be used as a template for detection. However, extracellular RNA (as well as other biomarkers disclosed herein) is often associated with one or more different types of membrane particles (ranging in size from 50-80 nm), exosomes (ranging in size from 50-100 nm), exosome-like vesicles (ranging in size from 20-50 nm), and microvesicles (ranging in size from 100-1000 nm). Other vesicle types may also be captured, including, but not limited to nanovesicles, vesicles, dexosomes, blebs, prostasomes, microparticles, intralumenal vesicles, endosomal-like vesicles or exocytosed vehicles. As used herein, the terms "exosomes" and "vesicles" shall be given their ordinary meaning and shall also be read to include any shed membrane bound particle that is derived from either the plasma membrane or an internal membrane. For clarity, the terms describing various types of vesicles shall, unless expressly stated otherwise, be generally referred to as vesicles or exosomes. Exosomes can also include cell-derived structures bounded by a lipid bilayer membrane arising from both herniated evagination (blebbing) separation and sealing of portions of the plasma membrane or from the export of any intracellular membrane-bounded vesicular structure containing various membrane-associated proteins of tumor origin, including surface-bound molecules derived from the host circulation that bind selectively to the tumor-derived proteins together with molecules contained in the exosome lumen, including but not limited to tumor-derived microRNAs or intracellular proteins. Exosomes can also include membrane fragments. Circulating tumor-derived exosomes (CTEs) as referenced herein are exosomes that are shed into circulation or bodily fluids from tumor cells. CTEs, as with cell-of-origin specific exosomes, typically have unique biomarkers that permit their isolation from bodily fluids in a highly specific manner. As achieved by several embodiments disclosed herein, selective isolation of any of such type of vesicles allows for isolation and analysis of their RNA (such as mRNA, microRNA, and siRNA) which can be useful in diagnosis or prognosis of numerous diseases.

Conventional methods for isolation of exosomes, or other vesicles, often involve ultracentrifugation (often multiple rounds) in order to separate the vesicles from other matter in a biological sample. Ultracentrifugation is accomplished through the use of specialized, expensive, and potentially hazardous equipment. Indeed, the tremendous rotational kinetic energy of the rotor in an operating ultracentrifuge makes the catastrophic failure of a spinning rotor a serious concern. Stresses associated with routine use eventually cause rotors to deteriorate and careful maintenance of rotors to prevent corrosion and to detect deterioration is necessary to avoid many hazards. However, even routine maintenance is beyond the capabilities of many persons trained in the use of an ultracentrifuge. Thus, maintenance can be expensive because of the specialized knowledge required to properly maintain and/or carefully repair such a potentially hazardous piece of laboratory equipment. Moreover, maintenance and needed repairs can result in delays for the user. Consequently, ultracentrifugation is sometimes an impractical or impossible technique for many laboratories.

Therefore, provided herein are devices, compositions, and methods for capture of exosomes, vesicles, and other circulating membrane bound, nucleic acid (including, but not limited to DNA, RNA, mRNA, microRNA, and siRNA) and/or protein-containing structures that are released from cells into biological fluids. Thus, in several embodiments the devices and methods as disclosed herein provide several advantages over traditional techniques for vesicle isolation, such as ultracentrifugation. In some embodiments, the devices and methods allow for the enrichment, concentration, and/or isolation of vesicles, exosomes, and/or biomarkers in samples by allowing for multiple filtrations of samples through the same filter. Consequently, increased amounts of material can be collected simply by applying multiple sample aliquots to a device. In some embodiments, samples can be manipulated while in and/or on the device. Thus, samples can be further purified prior to biomarker analysis by washing with solutions known to remove contaminants. In some embodiments, samples can be manipulated before, during, and/or after application to the device. Such manipulations can increase ultimate sample purity by removing potential contaminants. Such manipulations also allow the user to target different fractions of the same sample. This is particularly advantageous because a single device and method allows collection of various sized exosome or vesicles, whereas traditional techniques dispose of certain cellular (and/or non-cellular) fractions while in pursuit of a different particular fraction.

In several embodiments the devices and methods as disclosed herein are easier to use than traditional techniques for vesicle isolation, such as ultracentrifugation. Some embodiments do not require pretreatment of samples prior to use. Pretreatment can take many forms, including sample fractionation, precipitation of unwanted material, etc. For example, some embodiments allow for samples to be taken from donors and used "as-is" for isolation and testing of biomarkers. However, some embodiments allow a user to pretreat samples for certain reasons. These reasons include, but are not limited to, protocols to facilitate storage, facilitating biomarker detection, etc. Because the devices and methods utilize filters to capture vesicles, multiple samples can be run through the same filter and afford collection of all vesicles in one location, unlike traditional methods (e.g. ultracentrifugation) that can result in samples being collected in multiple tubes. Such traditional methods require manipulation by a user beyond what is minimally required by the disclosed methods and devices. Increased sample manipulation can increase the difficulty of isolating vesicles and increases the likelihood of user error, contamination, and/or sample loss.

In some embodiments, the devices disclosed herein are particularly efficient at processing samples. For example, the device can be configured in a multiwall plate format, allowing the high-throughput processing of samples. In some embodiments, the filter(s) employed in the device are particularly efficient at capturing vesicles from a sample. In some embodiments, the capture of the vesicles outperforms other methods. In some embodiments, the capture of vesicles is roughly equivalent to other methods, but allows for substantially greater release and/or isolation of DNA, RNA (including, but not limited to, mRNA, microRNA, and/or siRNA), or protein from the captured vesicles. In some embodiments, the cost of processing samples is reduced as compared to traditional methods. For example, several embodiments do not require specialized equipment (e.g., ultracentrifuge and associated rotors) whose startup and maintenance costs are quite high and whose operation renders them potentially hazardous. Some embodiments of the device are particularly advantageous because of the device's efficiency which allows for the use of low volumes of the biological sample. However, in some embodiments, repeated applications of aliquots of the biological sample will allow concentration (e.g., condensation, enrichment, and the like) of the vesicles in the sample (e.g., such embodiments are particularly useful for high volume-low vesicle concentration samples such as urine). In several embodiments, such concentrations allow for an enrichment of the biomarker of interest. Moreover, the devices disclosed herein are optionally self-contained, and therefore reduce the risk of contamination of the samples, and the possibility of the associated loss of DNA/RNA or protein that is to be analyzed (e.g., due to RNAses or proteases).

In several embodiments, devices comprising a sample loading region, a vesicle-capturing material, and a sample receiving region are provided. The devices allow a biological sample to be loaded into the sample loading region, passed over or through the vesicle-capturing material in order to trap, temporarily hold, or otherwise isolate the vesicles from the remainder of the components of the biological sample, which is received in the sample receiving region of the device. In some embodiments, the device comprises a single sample loading region, one or more vesicle-capturing materials, and a single sample receiving region. In several such embodiments, the devices are provided in a single use format (e.g., are pre-sterilized and disposable). However, in some embodiments, after capture of the vesicles and subsequent processing, the device can be cleaned and/or sterilized, and re-used. In several embodiments, the device comprises a plurality of sample loading regions, each associated with a corresponding plurality of vesicle-capturing material(s), and a corresponding plurality of sample receiving regions. In some embodiments, multi-well devices are configured with standard dimensions (e.g., those of a 96 well or 384 well plate) such that the device can be placed in standard laboratory equipment (e.g., a standard low-speed plate centrifuge). In still additional embodiments, the device is configured to interact with a device for high-throughput quantification of mRNA such as those described in U.S. Pat. No. 7,745,180, issued on Jun. 29, 2010, and is incorporated be reference herein.

In some embodiments, the vesicle-capturing material captures desired vesicles from a biological sample. In some embodiments, therefore, the vesicle-capturing material is selected based on the pore (or other passages through a vesicle-capturing material) size of the material. In some embodiments, the vesicle-capturing material comprises a filter. In some embodiments, the filter comprises pores. As used herein, the terms "pore" or "pores" shall be given their ordinary meaning and shall also refer to direct or convoluted passageways through a vesicle-capture material. In some embodiments, the materials that make up the filter provide indirect passageways through the filter. For example, in some embodiments, the vesicle-capture material comprises a plurality of fibers, which allow passage of certain substances through the gaps in the fiber, but do not have pores per se.

In those embodiments wherein the vesicle capture material comprises a filter, the type of filter may vary, depending on the application. As discussed above, the size (or quantity) of the vesicles to be captured is a consideration when choosing a filter. In other embodiments, a filter is chosen for overall vesicle retention capacity. In still additional embodiments, a filter is chosen for its efficiency in removing vesicles. Filters suitable for use in devices disclosed herein include, but are not limited to glass-like materials such as glass beads, glassfiber, silica, and the like; nitrocellulose; nylon; polyvinylidene fluoride (PVDF) and similar polymers; metal or nano-metal fibers; polystyrene; ethylene vinyl acetate or other co-polymers; natural fibers such as silk; alginate fiber; poly NZPA; or other fibrous materials. In some embodiments, two or more types of fibers may be used, for example by layering the materials over one another. In some embodiments, such devices may be more efficient, as each material used can be selected and/or positioned to optimize its filtration characteristics.

The vesicle retention rate of the vesicle-capture material is dependent on the dimensions of the vesicles to be captured. The rate is defined as the percentage retention of a vesicle (or particle) of a given size. For example a retention rate of 100% for vesicles would indicate that all of the particles of a particular size are captured within the material. In some embodiments, the retention rate of the vesicle-capture material is greater than 50%, 75%, 90% or 99% for vesicles having a diameter of from about 0.6 microns to about 1.5 microns in diameter. In several embodiments, retention rate is increased by the use of a plurality of layers of material, and/or modification of materials. In some embodiments, certain materials are used in a particular orientation in order to pre-filter larger cellular material or debris from a sample, which thereby further enhances the vesicle retention rate.

In some embodiments, the material is modified in order in enhance its vesicle capturing capability or to enable capture of different types of vesicles. In some embodiments, the material may be electrocharged (e.g., electrostatically charged), coated with hydrophilic or hydrophobic materials, chemically modified, or biologically modified. For example, in some embodiments, differential capture of vesicles is made based on the surface expression of protein markers and a complementary agent on the capture material that identifies that marker (e.g., an antibody that recognizes an antigen on a particular vesicle). In some embodiments, the markers are unique vesicle proteins or peptides. In some disease states, the markers may also comprise certain vesicle modifications, which, in some embodiments, are used to isolate particular vesicles. In such embodiments, the capture material is configured in a manner which allows for specific recognition of the vesicle modification. Modification of the vesicles may include, but are not limited to addition of lipids, carbohydrates, and other molecules such as acylated, formylated, lipoylated, myristolylated, palmitoylated, alkylated, methylated, isoprenylated, prenylated, amidated, glycosylated, hydroxylated, iodinated, adenylated, phosphorylated, sulfated, and selenoylated, ubiquitinated. In some embodiments, the capture material is configured to recognize vesicle markers comprising non-proteins such as lipids, carbohydrates, nucleic acids, RNA, mRNA, siRNA, microRNA, DNA, etc.

Depending on the configuration of the vesicle capturing device, various procedures may be used to pass a biological sample through the capture material. For example, in one embodiment, low speed centrifugation is used. In one embodiment, vacuum pressure is used. In one embodiment, positive pressure is used. In one embodiment, gravity is used. Combinations of these procedures may also be used. Thus, the vesicle capturing devices and associated methods described herein are highly versatile and suitable for use in a variety of laboratories.

The biological fluids from which vesicles can be captured using the devices disclosed herein include a variety of bodily fluids from a subject. As used herein, a "bodily fluid" shall be given its ordinary meaning and shall also refer to a sample of fluid isolated from anywhere in the body of the subject, including but not limited to, for example, blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. In some embodiments, the biological sample is preferably collected from a peripheral location or is naturally excreted or readily excreted by said subject.

After capture on the vesicle-capturing material, the vesicles are optionally washed, and are subsequently used for DNA or RNA extraction from the vesicles, and/or identification of proteins or other biomarkers on the vesicle. In several embodiments, multiple aliquots of a biological sample are passed through the device, thereby concentrating the vesicles from the sample. In some embodiments, the devices and methods disclosed herein lead to increased sensitivity in several diagnostic methods. For example, isolation of vesicles is useful in increasing sensitivity of diagnostic tests related to vascular disease, as is described in U.S. Provisional Patent Application No. 61/354,117, filed on Jun. 11, 2010, or related to kidney function, as is described in U.S. Provisional Patent Application No. 61/354,098, filed Jun. 11, 2010, the disclosures of each of which are incorporated by reference herein.

EXAMPLES

Example 1

Screening of Filters for the Capacity of Exosome Collection

One hundred (100) µL of rat plasma was applied to a vesicle-capture device as described herein in duplicate, where various vesicle capture materials (A-K shown in FIG. 1) were inserted at the bottom of each sample receiving well. The passing through fraction was collected and mixed with 2× Lysis Buffer. The resultant lysate was subject to poly(A)+ RNA preparation and cDNA synthesis using an oligo(dT)-immobilized microplate. Further information regarding the oligo(dT)-immobilized microplate can be found in U.S. Pat. No. 7,745,180, issued on Jun. 29, 2010, and Mitsuhashi et al., Quantification of mRNA in whole blood by assessing recovery of RNA and efficiency of cDNA synthesis. *Clin. Chem.* 52:634-642, 2006, the disclosure of each of which is incorporated be reference herein. Various mRNAs (group-specific component (gc), apolipoprotein H (apoh), solute carrier organic anion transporter family member 1b2 (slc1b2), plasminogen (plg), α1-microglobulin/bikunin precursor (ambp), and albumin (alb)) were then quantified by real time PCR. As a control, an aliquot of the original rat plasma sample was also mixed with 2× Lysis Buffer and mRNA was quantified simultaneously. The amount of each gene amplified is shown as 100% (dark horizontal line in FIGS. 1A-1F). The values of mRNA in the passing through fraction (e.g., the vesicle-depleted sample) were expressed as % Control by using the values of original plasma sample. Duplicate experiments measuring absorption (e.g., capture vesicles by the filters) are shown by the open circles (o) in FIGS. 1A-1F. The amounts of each of the 6 different mRNAs isolated and amplified from the passing through fraction were reduced when plasma was filtered. Lower values for the % Control value for each filter tested are representative of a greater degree of capture of vesicles by the filters (fewer vesicles present in passing through fraction yields lower generation of PCR product, and hence, a lower % Control). Accordingly, these results indicate that filters A: glassfiber (GF/F), B: nitrocellulose (NC), E: nano alumina fibers, and K: a leukocyte capture membrane perform well at capturing vesicles.

In several embodiments, merely capturing the vesicles from a biological sample is insufficient for use in a diagnostic or analytical method. Elution of the vesicles from the filter, extraction of DNA or RNA or protein from the captured vesicles, or use of the vesicles themselves in tests is desirable in some embodiments. To assess the ability to retrieve RNA from the captured vesicles, each of the filters was then treated with 1× Lysis Buffer, followed by poly(A)+ RNA preparation and cDNA synthesis on oligo(dT)-immobilized microplates, and real time PCR. As shown by the filled triangles (▲) in FIGS. 1A-1F, vesicle-associated mRNA was detected only from glassfiber (A), nitrocellulose (B), and leukocyte-capture membrane (K). Despite removing vesicles from the plasma, nano alumina fiber-trapped vesicles did not generate any PCR products, indicating that, despite lysis of the vesicles, RNA could not be recovered. Despite showing an absorption capacity similar to other filters, glassfiber filters unexpectedly yielded the greatest amount of associated PCR product generation (e.g., closest to 100% of Control for all six genes tested).

Example 2

Exosome Capture by Silica Particles

Figure 2:
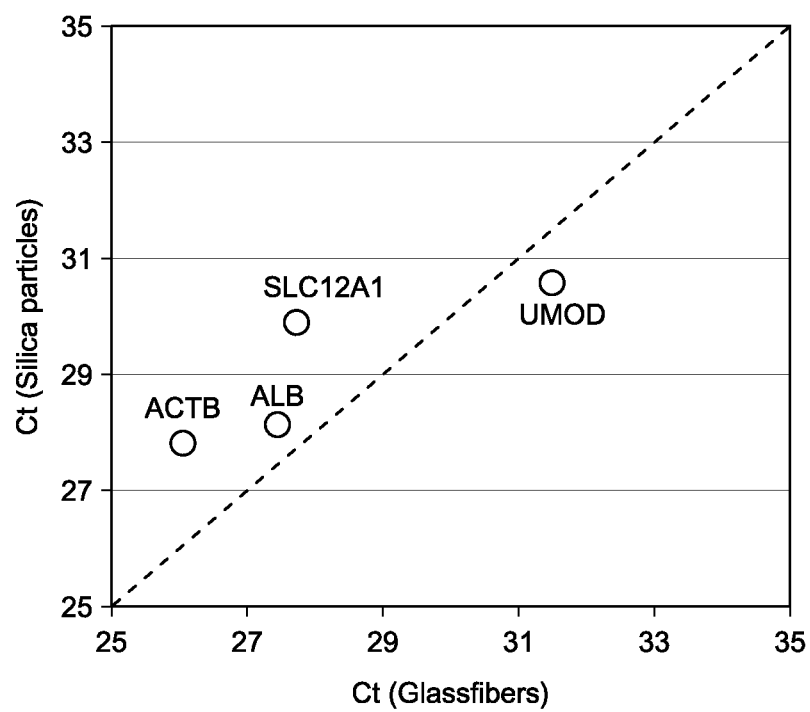
FIG. 2 compares exosome capture between glassfibers and silica particles.

Four mL urine samples from a single donor were applied to a vesicle-capture device as described herein (X-axis) or a spin column packed with silica particles (Qiagen RNeasy Mini-prep) (Y-axis). After centrifugation at 2,000×g for 5 min, Lysis Buffer was applied and incubated at 55° C. for 30 min. Lysate was then transferred to an oligo(dT)-immobilized microplate for mRNA purification, followed by cDNA synthesis and real time PCR, according to the established protocols (e.g., those described in U.S. Pat. No. 7,745,180). Experiments were performed in triplicate. As shown in FIG. 2, mRNA was detected using either glassfibers or silica particles, although glassfibers showed better recovery than that of silica particles.

Example 3

Exosome Capture from Saliva

Ten, 1000 µL, saliva samples from a single donor were applied to a vesicle-capture device as described comprising glassfiber filters. After centrifugation at 2,000×g for 5 min, Lysis Buffer was applied and incubated at 55° C. for 30 min.

Figure 3:
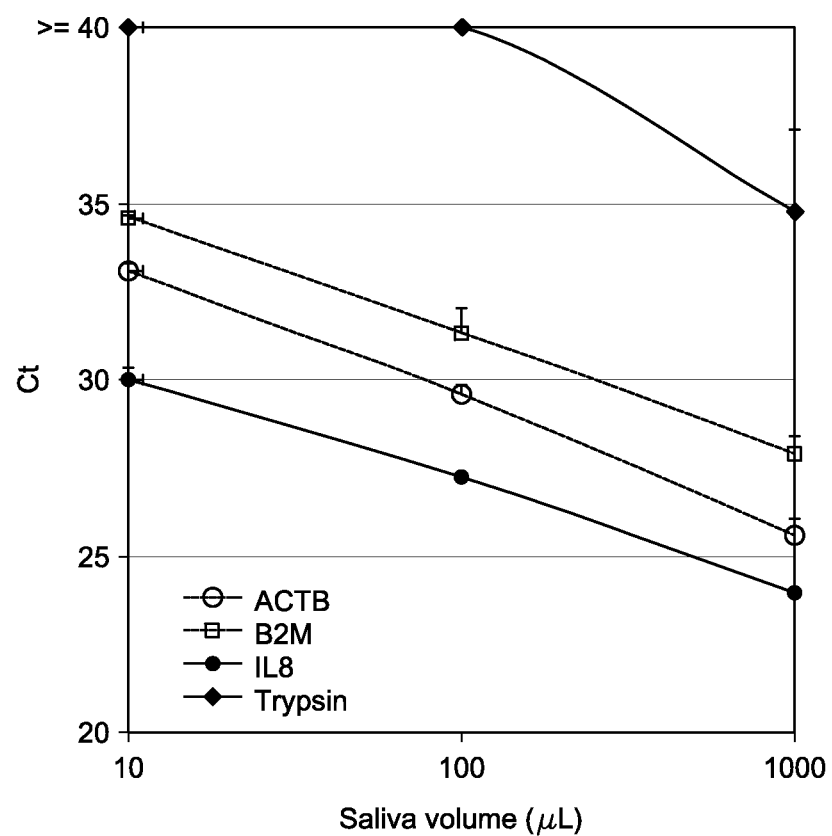
FIG. 3 depicts an mRNA analysis of saliva exosomes captured by glassfiber filters.
Figure 4A:
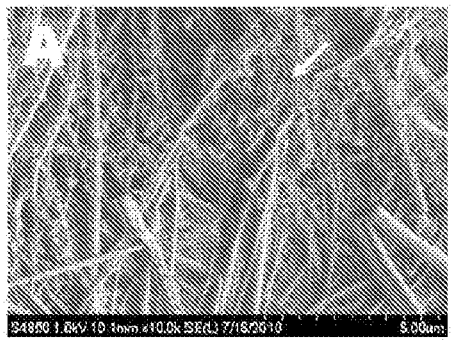
FIGS. 4A-4F depict scanning electron analysis of exosomes captured from a urine sample.
Figure 4B:
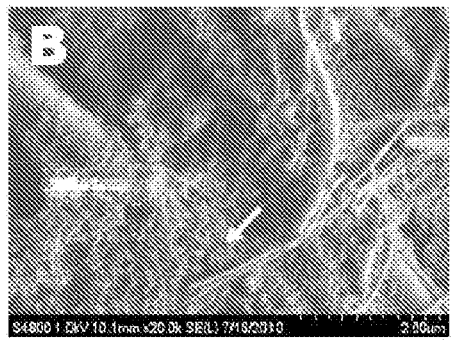
Figure 4C:
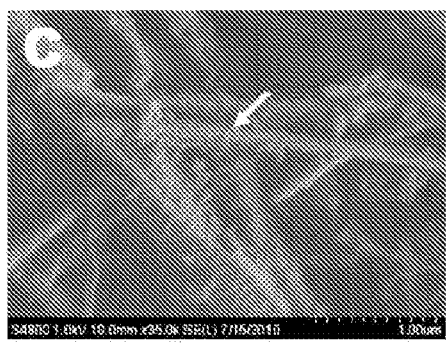
Figure 4D:
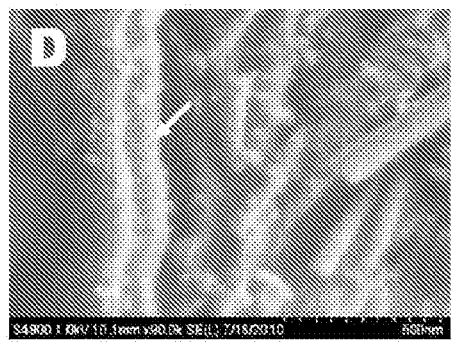
Figure 4E:
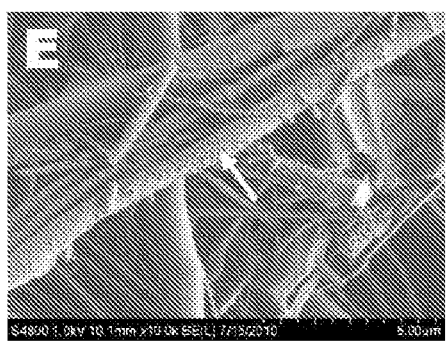
Figure 4F:
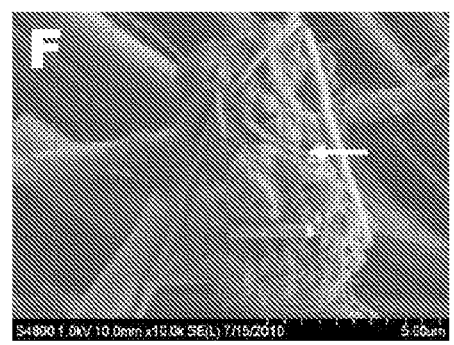

Lysate was then transferred to an oligo(dT)-immobilized microplate for mRNA purification, followed by cDNA synthesis and real time PCR, according to protocol discussed above and further described in U.S. Pat. No. 7,745,180. As shown in FIG. 3, various mRNAs (ACTB, B2M, IL8, and trypsin) were detected from saliva. Consequently, the filter-based methods and devices disclosed herein are capable of capturing exosomes from saliva samples without the need for costly ultracentrifugation and with decreased risk of contamination (due to the more streamlined protocol).

Example 4

Visualization of Captured Materials on Glassfiber Filter

Human urine was applied to a glassfiber filter and subsequently washed with water. Vesicle-laden filters were then analyzed by scanning electron microscope (SEM). As shown in FIG. 4, small vesicle-like materials were trapped by the mesh of filters (white arrows in 4A and 4B). Vesicles also adhered to the fiber surfaces (white arrows in 4C and 4D). Occasionally, the aggregates of vesicles were also trapped by the filter (white arrows in 4E and 4F). According to the method discussed above, it was confirmed that this filter at least contained β-actin (ACTB), solute carrier family 12A1 (SLC12A1), and uromodulin (UMOD) mRNA, which are all markers that could be used as diagnostic or control markers from a urine sample. Thus, the devices and methods disclosed herein are well suited for capture of vesicles from urine samples without the need for costly ultracentrifugation and with decreased risk of contamination.

Example 5

Scanning Electron Microscopic Analysis of Exosomes Capture from Urine

Figure 5:
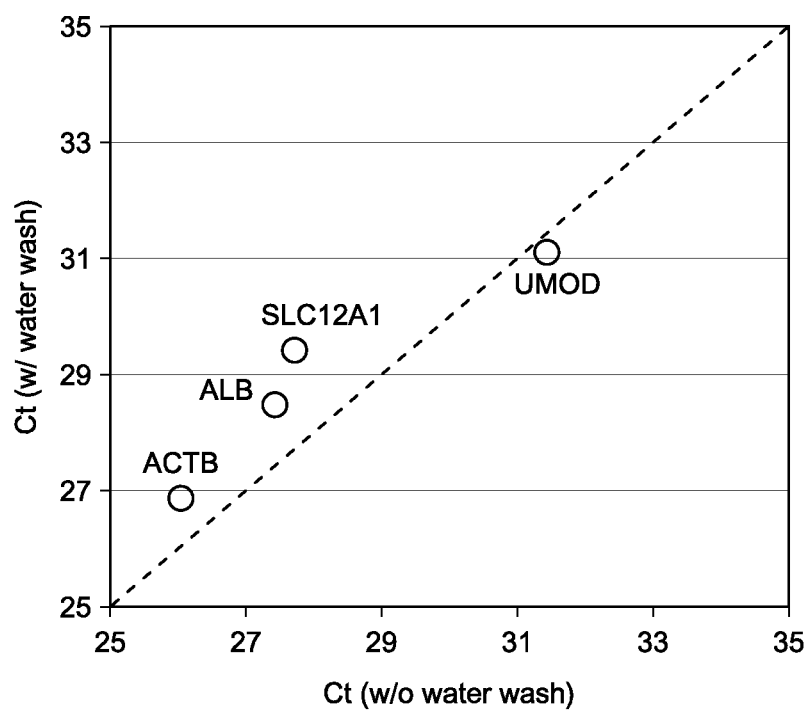
FIG. 5 depicts an mRNA analysis of urine exosomes and compares the effects of water washing.

Urine contains various salts in addition to useful biomarkers. These salts, especially salt crystals, may mask the visualization of exosomes in SEM visualization. Consequently, before undertaking SEM analysis of exosomes on a filter, in several embodiments, the filter should be washed with water to eliminate any salts. However, in other embodiments, salts do not interfere, and filter washing is not required. As shown in FIG. 5, various mRNAs (ACTB, ALB, SLC12A1, and UMOD) were quantified from a glassfiber filterplate with (Y-axis) or without (X-axis) a water wash. The results indicate that washing with water did not significantly affect the detection of mRNA. Consequently, exosomes can be isolated with fewer impurities and lower levels of contamination as compared to traditional methods of exosome isolation (e.g., those that require ultracentrifugation, multiple solute transfers to multiple tubes, and/or multiple rounds of purification). In several embodiments, depending upon the source of the biological sample, washings with water and additional fluids is incorporated to further remove impurities and afford enriched, highly pure exosome capture.

Figure 6A:
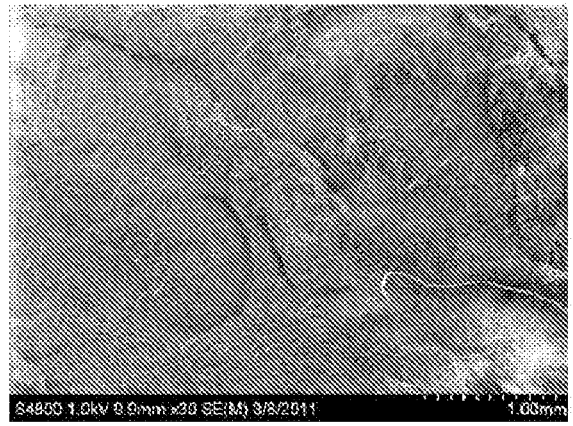
FIGS. 6A-6C depict low magnification scanning electron analysis of exosomes captured from a urine sample.
Figure 6B:
Figure 6C:

SEM analysis was then performed and the low magnification results are provided in FIG. 6. FIG. 6A shows plain glassfiber before urine application, FIG. 6B shows urine application followed by water wash of the filter, and FIG. 6C shows urine application followed by lysis buffer application to the filter, 55° C. incubation for 30 min, and a subsequent water wash. Bright corner and side edge in FIG. 6A are artifact and were due to charging. The bright areas in B were due to urine application. C was similar to A except for a small area that appears to be a remnant after lysis and washing. This analysis indicates that the filter-based methods and devices afford not only the efficient capture of exosomes and similar condensed materials, but also allow for the easy and efficient manipulation of exosomes on the filter. This ease and efficiency is particularly advantageous for sample analyses and diagnostic methods and is amenable to high-throughput variations of analyses and diagnostic methods.

Example 6

Comparison to Ultracentrifugation Method

Figure 7A:
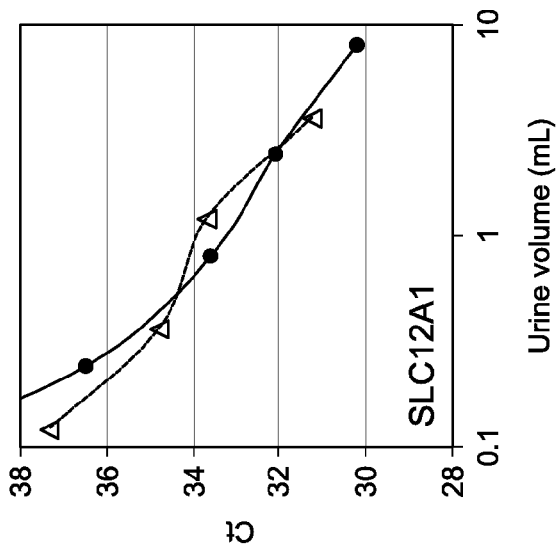
FIGS. 7A-7C depict a comparison of the efficiency of exosome capture on filters as compared to established ultra-centrifugation methods.
Figure 7B:
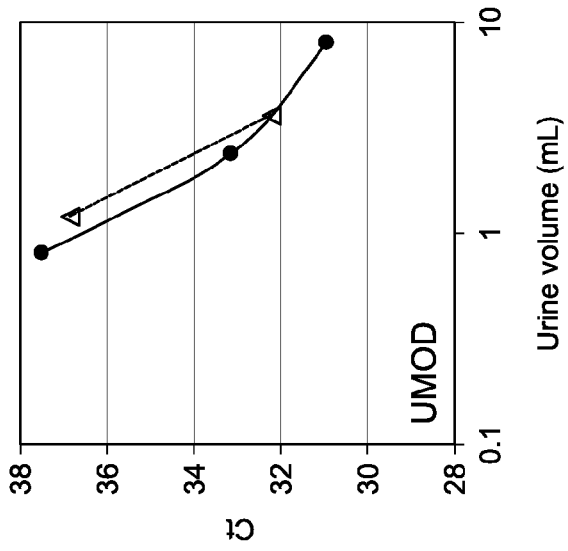
Figure 7C:
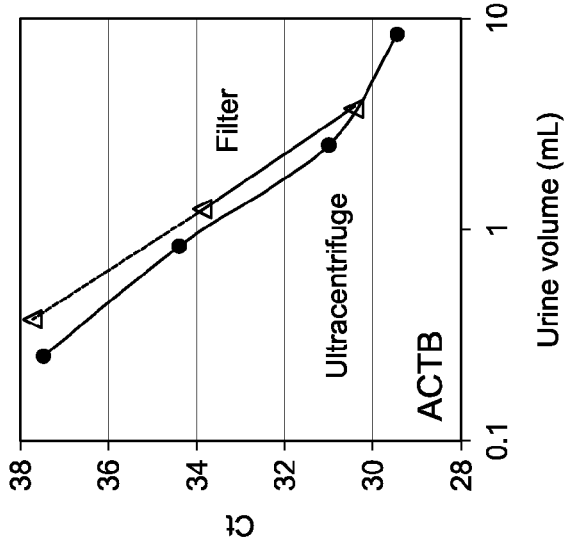

Various volumes of human urine were applied to glassfiber filters, followed by mRNA quantification as described above. As shown in FIG. 7 (Δ), ACTB, UMOD, and SLC12A1 mRNA were quantified in a dose dependent manner. The maximal urine volume applied to the filter was 3 mL (to a single well of a 96-well filterplate). In parallel, aliquots of the same urine aliquots subjected to an art-established ultracentrifugation protocol (40,000×g for 30 min) to isolate vesicles. The resultant vesicle pellets were dissolved in 1× Lysis buffer, followed by mRNA preparation, cDNA synthesis and real time PCR (●). As shown in FIG. 7, the filter-based methods and devices yielded results that were not significantly different than the traditional ultracentrifuge method. However, the above discussion illustrates that unlike ultracentrifugation, the filter-based methods and devices are amenable to manipulation during sample isolation or enrichment. These manipulations include, but are not limited to water washing, buffer washing, lysis on the filter, etc. Consequently, the filter-based methods represent a highly versatile and easy to use alternative to ultracentrifugation that does not sacrifice sensitivity in the detection of the desired biomarker.

Example 7

Determination of Zeta Potential of Vesicle Capture Materials

Figure 8B:
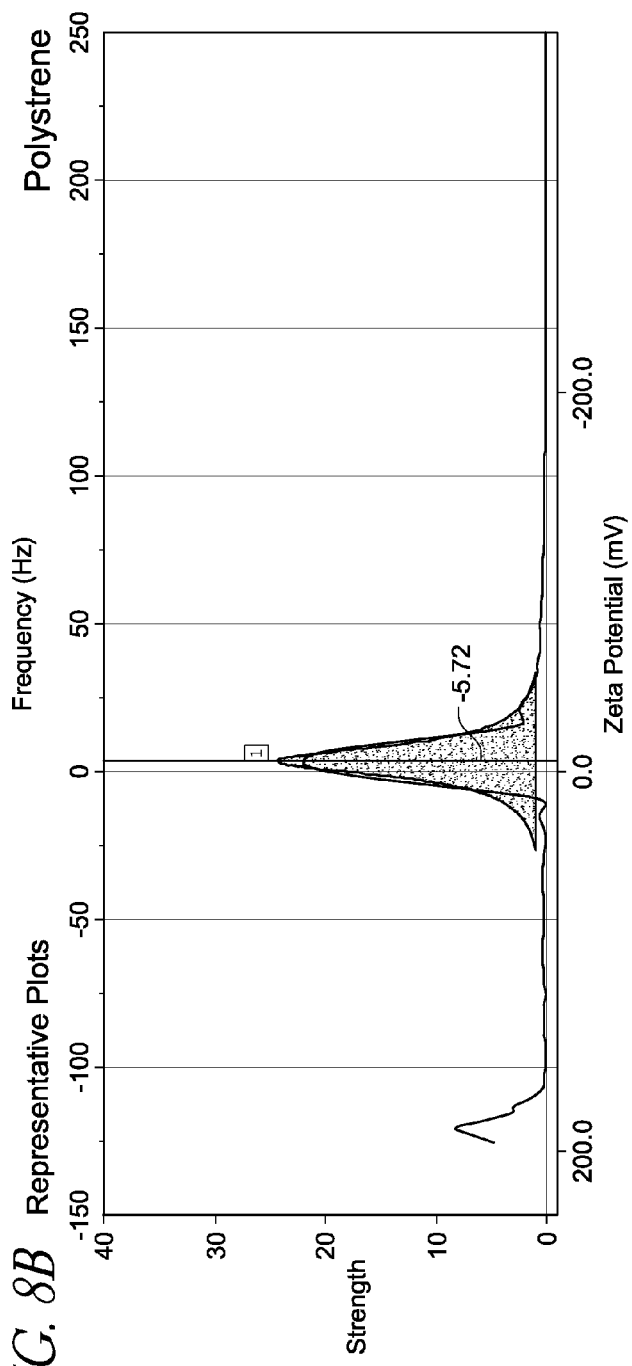
Figure 9B:
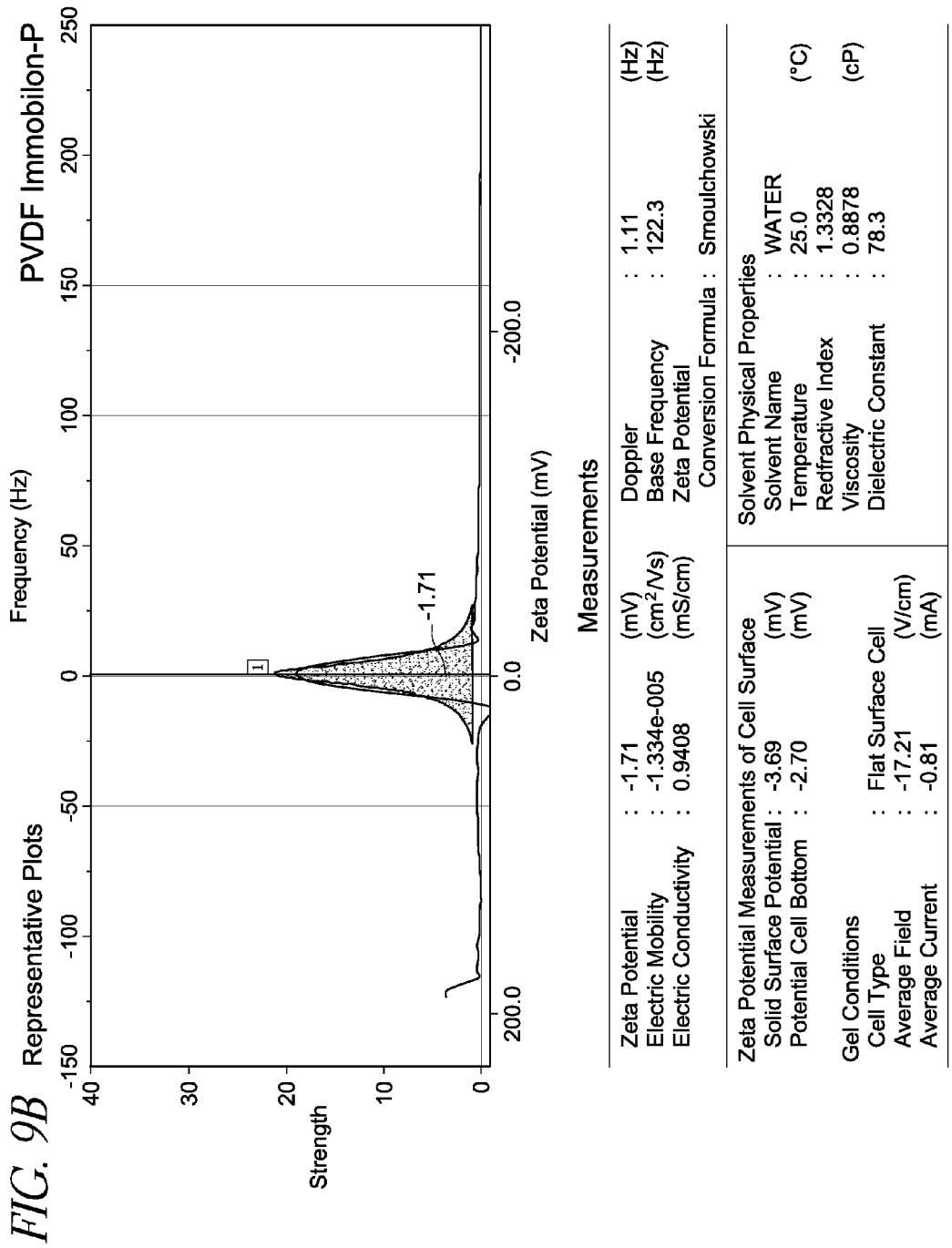
Figure 11B:
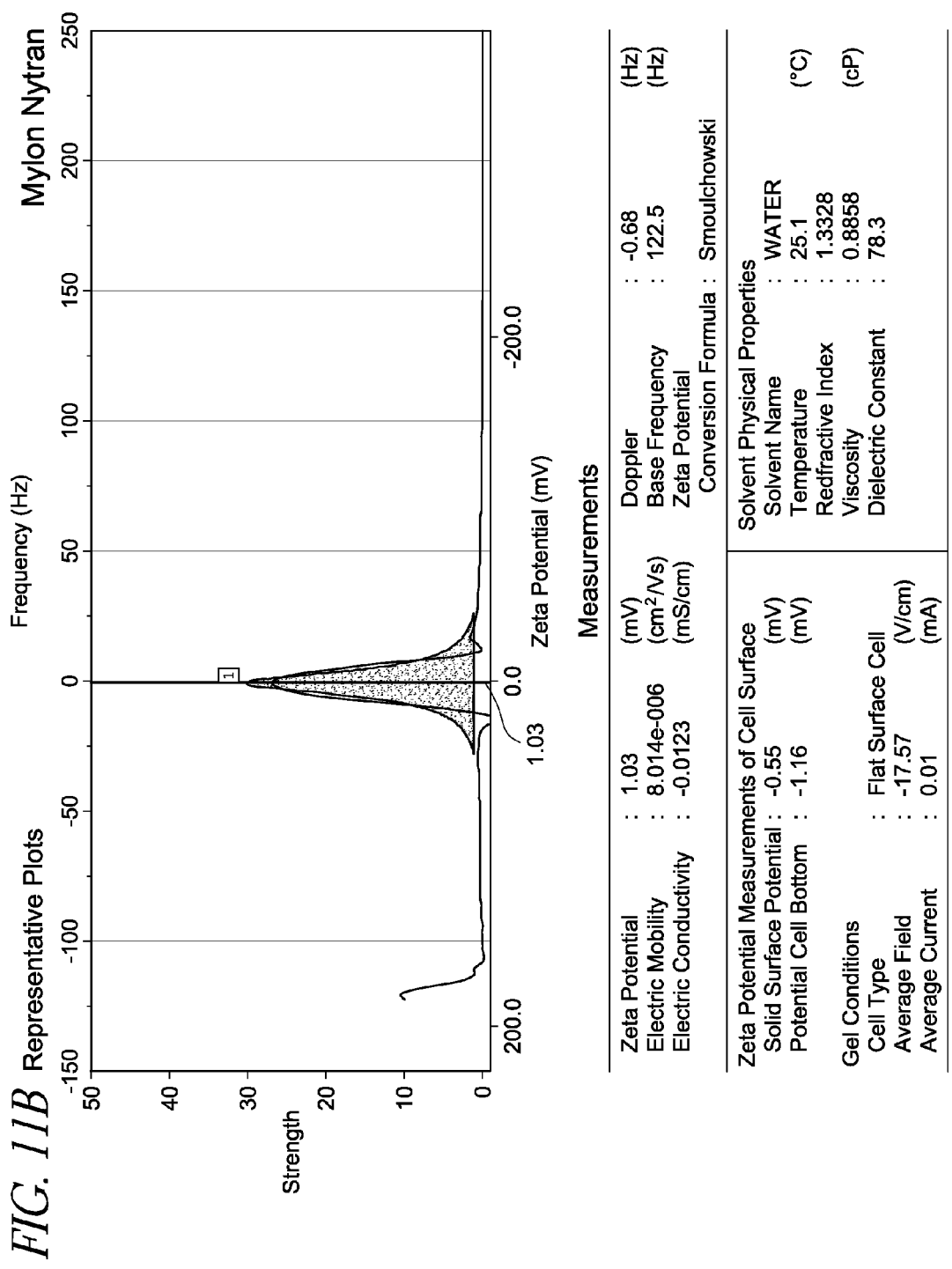

The zeta potential of a material is one measure of the ability that material to attract particles. Based on the disclosure above, the ability to attract (e.g., filter) vesicles from a biological fluid is beneficial in analysis of vesicle-associated biomarkers. While the overall surface charge on a vesicle will depend on the lipid and protein make-up of the vesicle, as well as the pH of the fluid in which the vesicle is contained, the vesicle capture media can be chosen (and or modified) in order to provide improved attractive forces to the vesicles. As shown in FIGS. 8A-8B, the zeta potential for polystyrene vesicle capture material was calculated as negative 5.72 mV. FIGS. 9A-9B, depict the zeta potential for PVDF Immobilon-P vesicle capture material, which was calculated as negative 1.71 mV. FIGS. 10A-10B depict the zeta potential for glassfiber, which was calculated as negative 2.60 mV. Finally, FIGS. 11A-11B depict the zeta potential for mylon nytran, which was calculated as positive 1.03 mV. As also shown in FIGS. 8B, 9B, 10B, and 11B, each vesicle capture material showed a varied strength of attraction (y-axis), which is representative of the ability of the material to hold the vesicle. These data suggest that, depending on the charge of the vesicles to be captured, certain materials (or combinations of materials) may be optimally suited for a certain vesicle type. For example, if a target vesicle is positively charged, a polystyrene vesicle capture material may provide the greatest attractive forces to capture the vesicle from the fluid. As discussed above, however, release of the vesicle from the vesicle capture material is also important in some embodiments. Thus, the attractive forces (the zeta potential), in several embodiments, are balanced with the strength of attraction (negatively correlated with the release of vesicles from the material). In some embodiments, the vesicle capture materials may be modified (as discussed above) in order to tailor their vesicle-capturing profile.

What is claimed is:

1. A method of isolating vesicles from biological fluid, comprising:
   (a) obtaining a biological fluid sample comprising vesicles having a diameter of less than 0.5 micrometers;
   (b) loading at least a portion of said biological fluid sample into a sample loading region of a vesicle capture device, said portion of said biological fluid sample comprising blood plasma and vesicles having a diameter of less than 0.5 micrometers;
   (c) passing said portion of said biological fluid sample from said sample loading region through a vesicle-capture material in said vesicle capture device, said vesicle-capture material comprising at least a first layer and a second layer, both of glassfiber, at least a portion of said vesicles having a diameter of less than 0.5 micrometers adsorbing to and being retained by the vesicle-capture material, thereby producing a supernatant,
   wherein said first layer is closer to said sample loading region than said second layer,
   wherein said first layer has a porosity configured to capture material that is 1.6 micrometers or greater in diameter, wherein said second layer has a porosity configured to capture material that is 0.6 micrometers to 0.8 micrometers or greater in diameter; and
   (d) passing said supernatant to a sample receiving region of said vesicle capture device, thereby isolating vesicles from the biological fluid sample.

2. The method of claim 1, wherein said vesicle-capture material further comprises a non glass-like material.

3. The method of claim 2, wherein said non glass-like material comprises nitrocellulose.

4. The method of claim 1, wherein said passings are accomplished through the application of vacuum pressure to the device.

5. The method of claim 1, wherein said passings are accomplished through the application of positive pressure to the device.

6. The method of claim 1, wherein said passings are accomplished through low-speed centrifugation of the device.

7. The method of claim 1, wherein said vesicle capture device is configured in a multi-well plate format.

8. The method of claim 1, further comprising eluting said vesicles from said vesicle-capture material.

9. A method of isolating vesicle-associated RNA from a biological fluid comprising vesicles, the method comprising:
   (a) obtaining a biological fluid sample comprising blood plasma and vesicles having a diameter of less than 0.5 micrometers;
   (b) loading said biological fluid sample into a sample loading region of a vesicle capture device;
   (c) passing said biological fluid sample from said sample loading region through a vesicle-capture material in said vesicle capture device, said vesicle-capture material comprising at least a first layer and a second layer, both of glassfiber, thereby producing a supernatant,
   wherein said first layer has a porosity configured to capture particles that are 1.6 micrometers or greater in diameter, and
   wherein said second layer has a porosity configured to capture particles that are 0.6 micrometers to 0.8 micrometers or greater in diameter;
   (d) passing said supernatant to a sample receiving region of said vesicle capture device and discarding the supernatant,
   wherein said passings result in capture of at least a portion of said vesicles having a diameter of less than 0.5 micrometers from said biological fluid sample on or in said vesicle-capture material;
   (e) lysing said vesicle on or in said vesicle-capture material to create a lysate; and
   (f) collecting the lysate from both of said first and second layers of said vesicle-capture material into a single receiving region, thereby isolating vesicle-associated RNA from the biological fluid sample comprising vesicles.

* * * * *